(12) United States Patent
Pawel-Rammingen et al.

(10) Patent No.: US 7,666,582 B2
(45) Date of Patent: Feb. 23, 2010

(54) **IDES, AN IGG-DEGRADING ENZYME OF *STREPTOCOCCUS PYOGENES***

(75) Inventors: Ulrich Von Pawel-Rammingen, Lund (SE); Bjorn Johansson, Lund (SE); Lars Björck, Lund (SE)

(73) Assignee: Hansa Medical Research AB, Lund (SE)

( * ) Notice: Subject to any disclaimer, the term of this patent is extended or adjusted under 35 U.S.C. 154(b) by 226 days.

(21) Appl. No.: 10/499,143

(22) PCT Filed: Dec. 17, 2002

(86) PCT No.: PCT/EP02/14427

§ 371 (c)(1),
(2), (4) Date: Nov. 30, 2004

(87) PCT Pub. No.: WO03/051914

PCT Pub. Date: Jun. 26, 2003

(65) Prior Publication Data

US 2005/0119464 A1    Jun. 2, 2005

(30) Foreign Application Priority Data

Dec. 18, 2001    (GB) .................................. 0130228.0

(51) Int. Cl.
*C12Q 1/00*    (2006.01)
*G01N 33/53*    (2006.01)
*C07H 21/04*    (2006.01)
*C07K 14/195*    (2006.01)
*C12P 21/04*    (2006.01)

(52) U.S. Cl. ........................... 435/4; 435/7.1; 435/69.1; 435/69.7; 435/253.4; 435/320.1; 536/23.7; 530/350

(58) Field of Classification Search .................. 435/7.1, 435/69.1, 69.7, 252.3, 320.1; 530/387.1, 530/395; 536/23.7
See application file for complete search history.

(56) References Cited

U.S. PATENT DOCUMENTS 5,976,542 A    11/1999    Weiser et al.
2007/0237784 A1    10/2007    Von Pawel-Rammingen et al.

FOREIGN PATENT DOCUMENTS

WO    WO 02/50107    6/2002

OTHER PUBLICATIONS

Infection and Immunity, May 2003, vol. 71, No. 5 p. 2881-2884.*
Berasain et al Molecular and Biochemical Parasitology vol. 130, Issue 1, Aug. 11, 2003, pp. 23-29.*
Lei et al Nature Medicine 7, 1298-1305 (2001) ; Rammingen et al EMBO 2002, 21, 1607-1615.*
Collin etal EMBO 2001, 20, 3046-3055.*

Ferretti et al; "Complete Genome Sequence of an M1 Strain of *Streptococcus pyogenes*"; Proceedings of the National Academy of Sciences of USA, National Academy of Science, Washington, US, vol. 98, No. 8; Apr. 10, 2001, pp. 4658-4663, XP002168716 & Database EMBL 'Online, EBI, April 16, 2001, Ferretti et al; "*Streptococcus pyogenes* M1 Gas Strain SF370, Section 65 of 167 of the Complete Genome"; XP00224549.
Kawabata et al; "A Novel, Anchorless *Streptococcal* Surface Protein That Binds to Human Immunoglobulins"; Biochemical and Biophysical Research Communications, 200, vol. 296, No. 5, pp. 1329-1333, XP002243546 & Database EMBL Online, EBI, Jan. 12, 2001, Tamura et al; "*Streptococcus pyogenes* sib38 Gene"; XP002243550.
Lei et al; "Evasion of Human Innate and Acquired Immunity by a Bacterial Homolog of CD11b That Inhibits Opsonophagocytosis"; Nature Medicine, vol. 7, No. 12, Dec. 2001, pp. 1298-1305, XP002243547.
Von Pawel-Rammingen et al; "IdeS, A Novel *Streptococcal* Cysteine Proteinase With Unique Specificity for Immunoglobulin G"; EMBO Journal, vol. 21, No. 7, Apr. 2, 2002, pp. 1607-1615, XP002243548.
Database EMBL Online, EBI, Jul. 1, 2002, Telford et al.; "*Streptococcus polynucleotide* Seq ID No: 7763"; Retrieved form EMBL Database Accession No. ABN69925 XP002243551 & WO 02/34771, May 2, 2002.
Database EMBL Online, EBI, Sep. 24, 2002; Martin et al; "DNA Encoding *Streptococcus pyogenes* Strain M1 BVH-P6"; Retrieved from EMBL Database Accession No. ABK95354, XP002243552 & WO 02/50107, Jun. 27, 2002.
Von Pawel-Rammingen et al; "IdeS and SpeB: Immunoglobulin-Degrading Cysteine Proteinases of *Streptococcus pyogenes*"; Current Opinion in Microbiology, vol. 6, No. 1, Feb. 20, 2003, pp. 50-53, XP001152575.
Collin and Olsen, "EndoS, a novel secreted protein from *Streptococcus pyogenes* with endoglycosidase activity on human IgG", The EMBO Journal 29(12):3046-3055 (2001).
Collin and Olsen, "Effect of SpeB and EndoS from *Streptococcus pyogenes* on Human Immunoglobulins", Infection and Immunity 69(11):7187-7189 (2001).
Frank, M.M., "Annihilating host defense", Nature Medicine 7(12):1285-1286 (2001).
Lei et al, "Identification and Immunogenicity of Group A *Streptococcus* Culture Supernatant Proteins", Infection and Immunity 68(12):6807-6818 (2000).
Arnaout et al, "Amino Acid Sequence of the Alpha Subunit of Human Leukocyte Adhesion Receptor Mo1 (Complement Receptor Type 3)", J. Cell Biol. 106:2153-2158 (1988).
Björck et al, "Bacterial growth blocked by a synthetic peptide based on the structure of a human proteinase inhibitor", Nature 337:385-386 (1989).

(Continued)

*Primary Examiner*—Robert B Mondesi
*Assistant Examiner*—Padma V Baskar
(74) *Attorney, Agent, or Firm*—Nixon & Vanderhye P.C.

(57) ABSTRACT

A polypeptide isolated from *S. pyogenes* is described, having IgG cysteine protease activity. The protease is designated IdeS, Immunoglobulin G-degrading enzyme of *S. pyogenes*. A polypeptide comprises SEQ ID NO: 1 and variants and fragments thereof having IgG cysteine protease activity or the ability to generate an immune response against *S. pyogenes* in an individual. Polynucleotides encoding these polypeptides and the polypeptides may be used in generating an immune response in an individual. IdeS protease inhibitors may be used in the treatment of *S. pyogenes* infection.

5 Claims, 4 Drawing Sheets

OTHER PUBLICATIONS

Elliot, S.D., "A Proteolytic Enzyme Produced by a Group A Streptococci with Special Reference to its Effect on the Type-Specific M Antigen", J. Exp. Med. 81:573-592 (1945).

Kagawa et al, "Crystal structure of the zymogen form of the group A Streptococcus virulence factor SpeB: An integrin-binding cysteine protease", Proc. Natl. Acad. Sci. USA 97(5):2235-2240 (2000).

Kapur et al, "Cleavage of interleukin 1β (IL-1β) precursor to produce active IL-1β by a conserved extracellular cysteine protease from *Streptococcus pyogenes*", Proc. Natl. Acad. Sci. USA 90:7676-7680 (1993).

Burns et al, "Activation of a 66-Kilodalton Human Endothelial Cell Matrix Metalloprotease by *Streptococcus pyogenes* Extracellular Cysteine Protease", Infection and Immunity 64(11):4744-4750 (1996).

Herwald et al, "Streptococcal Cysteine Proteinase Release Kinins: a Novel Virulence Mechanism", J. Exp. Med. 184-665-673 (1996).

Berge and Björck, Streptococcal Cysteine Proteinase Releases Biologically Active Fragments of Streptococcal Surface Proteins, The Journal of Biological Chemistry 270(17):9862-9867 (1995).

Roe et al, "*Streptococcus pyogenes* Genome Sequencing Strain M1 GAS", http://www.genome.ou.edu/strep.html (2001).

Rawlings and Barrett, "Families of Cysteine Peptidases", Methods Enzymol. 244:461-486 (1994).

Suvorov and Ferretti, "Physical and Genetic Chromosomal Map of an M Type 1 Strain of *Streptococcus pyogenes*", Journal of Bacteriology 178(18):5546-5549 (1996).

Von Pawel-Rammingen et al, Office Action dated Sep. 11, 2009, U.S. Appl. No. 11/730,659.

Houghten et al, "Relative Importance of Position and Individual Amino Acid Residues in Peptide Antigen-Antibody Interactions: Implications in the Mechanism of Antigenic Drift and Antigenic Shift", Edited by Fred Brown: Cold Spring Harbor Laboratory), Vaccines, pp. 21-25 (1986).

Holmes, "PSMA specific antibodies and their diagnostic and therapeutic use", Exp. Opin. Invest. Drugs 10(3):511-519 (2001).

Greenspan et al, "Defining epitopes: It's not as easy as it seems", Nature Biotechnology 7:936-937 (1999).

Accession No. Q9F1R7, Mar. 1, 2001.

* cited by examiner

IDES, AN IGG-DEGRADING ENZYME OF *STREPTOCOCCUS PYOGENES*

This application is the US national phase of international application PCT/EP02/14427 filed 17 Dec. 2002, which designated the US. PCT/EP02/14427 claims priority to GB Application No. 0130228.0 filed 18 Dec. 2001. The entire contents of these applications are incorporated herein by reference.

FIELD OF THE INVENTION

The invention relates to a new *Streptococcus pyogenes* protein which displays IgG cysteine protease activity. The invention further relates to the treatment, vaccination and diagnosis of *S. pyogenes* infection and to the development of new tools for biotechnology.

BACKGROUND OF THE INVENTION

*S. pyogenes* (Group A streptococcus) is an important human bacterial pathogen best known as the cause of skin and throat infections. Streptococcal infections vary in severity from relatively mild diseases, like impetigo and pharyngitis, to serious life threatening conditions such as septicemia, necrotizing fascitis, and streptococcal toxic-shock syndrome (Bisno and Stevens, 1996; Cunningham, 2000). Sequelae to *S. pyogenes* skin and throat infections include serious conditions such as acute rheumatic fever and post-streptococcal glomerulonephritis.

*S. pyogenes* expresses cell wall-anchored surface proteins with the ability to interact with abundant extracellular human proteins such as albumin, IgG, IgA, fibrinogen, fibronectin, and $\alpha_2$-macroglobulin (for references see Navarre and Schneewind, 1999). Many of these protein-protein interactions are mediated by members of the M-protein family.

SUMMARY OF THE INVENTION

The present inventors have identified, purified and characterised a new extracellular cysteine protease produced by *S. pyogenes*. The protease, designated IdeS (Immunoglobulin G-degrading enzyme of *S. pyogenes*) displays a high specificity for IgG, cleaving in the hinge region of the immuno globulin. The protease cleaves not only IgG bound to the bacterial surface by IgGFc-binding proteins, but also opsonising IgG, and so appears to have a role in helping *S. pyogenes* to evade the host immune system. The inventors have shown that IdeS is expressed in both the logarithmic and stationary phases of bacterial growth, and in a number of clinically relevant *S. pyogenes* strains, including those of the M1, M12 and M55 serotypes. Antibodies to IdeS were found in individuals suffering from *S. pyogenes* infection, with those found in convalescent sera capable of blocking IdeS enzymatic activity. IdeS is therefore of use in the treatment and diagnosis of conditions associated with *S. pyogenes* infection. The protease is also useful for developing new biotechnological tools.

Accordingly the invention provides a polypeptide comprising:

(a) the amino acid sequence of SEQ ID NO: 1;

(b) a variant thereof having at least 50% identity to the amino acid sequence of SEQ ID NO: 1 and having IgG cysteine protease activity; or (c) a fragment of either thereof having IgG cysteine protease activity.

The invention also provides a polypeptide for use in generating an immune response in an individual comprising:

(a) the amino acid sequence of SEQ ID NO: 1;

(b) a variant thereof having at least 50% identity to the amino acid sequence of SEQ ID NO: 1 and having IgG cysteine protease activity; or (c) a fragment of either thereof which is capable of generating an immune response to *S. pyogenes* in an individual.

In another aspect the invention provides a polynucleotide which comprises:

(a) SEQ ID NO: 3 or a complementary sequence thereto;

(b) a sequence which hybridises under stringent conditions to the sequence defined in (a);

(c) a sequence which is degenerate as a result of the genetic code to a sequence as defined in (a) or (b);

(d) a sequence having at least 60% identity to a sequence as defined in (a), (b) or (c); or (e) a fragments of any of the sequences (a), (b), (c) or (d), and which encodes a polypeptide having IgG cysteine protease activity or capable of generating an immune response against *S. pyogenes* in an individual.

The invention also relates to expression vectors comprising a polynucleotide of the invention and host cells transformed with such expression vectors.

In another aspect, the invention relates to a method for identifying an agent that modulates IgG cysteine protease activity of a polypeptide having the amino acid sequence of SEQ ID NO: 1 comprising:

(i) contacting a polypeptide as defined above and IgG with a test substance under conditions that would permit IgG cysteine protease activity in the absence of the test substance; and (ii) determining thereby whether the test substance modulates the said activity.

Inhibitors of the cysteine protease of the invention, for example identifiable by the other method are provided for use in the treatment of *S. pyogenes* infection.

The polypeptides of the invention may be used in a method of generating Fc or Fab fragments of IgG comprising contacting IgG with the polypeptide.

The invention also relates to a method of generating an immune response in an individual comprising administering a polypeptide, polynucleotide or expression vector of the invention. Preferably, the polypeptide or polynucleotide is used to generate a protective immune response. Methods of treating *S. pyogenes* infection are also described, comprising administering an antibody or an IdeS protease inhibitor to an individual.

BRIEF DESCRIPTION OF THE SEQUENCES

Figure 1:
FIG. 1 shows the amino acid sequence found in the hinge region of human IgG including the cleavage site for IdeS.

SEQ ID NO:1 is an amino acid sequence encoding IdeS isolated from *S. pyogenes* AP1.

SEQ ID NO:2 is an amino acid sequence encoding IdeS isolated from *S. pyogenes* AP1, including a putative signal sequence.

SEQ ID NO:3 is nucleic acid sequence encoding IdeS, isolated from *S. pyogenes* AP1 (including a signal sequence).

SEQ ID NO:4 is PCR primer Ide1.

SEQ ID NO:5 is PCR primer Ide2.

SEQ ID NO:6 is PCR primer Ide5x

SEQ ID NO:7 is PCR primer Ide3x

SEQ ID NO:8 is N terminal amino acid sequence of an IdeS human IgG cleavage product.

SEQ ID NO:9 is N terminal amino acid sequence of IdeS isolated from *S. pyogenes* AP1.

SEQ ID NO:10 is a cell wall attachment signal found in a number of bacterial proteins.

DETAILED DESCRIPTION OF THE INVENTION

The invention provides certain polypeptides. In particular, in accordance with the invention these polypeptides may be used in the prophylaxis and diagnosis of infection by *S. pyogenes* strains.

Polypeptides in accordance with the invention are those which comprise the amino acid sequence of SEQ ID NO:1 and display IgG cysteine protease activity, together with functional variants, derivatives and fragments thereof. The invention also relates to variants and fragments of SEQ ID NO: 1 which have the ability to generate an immune response in an individual and in particular those which generate antibodies having the ability to block the enzymatic activity of IdeS, or to generate a protective immune response. Preferably, the polypeptide comprises the sequence of SEQ ID NO:1. The polypeptide may additionally include a signal sequence as in SEQ ID NO:2.

Variant polypeptides are those for which the amino acid sequence varies from that in SEQ ID NO:1, but which retain the same essential character or basic functionality as IdeS. The variant polypeptides may therefore display IgG cysteine protease activity or the ability to generate an immune response in an individual. In particular such variants include those which are able to generate antibodies having the ability to block the enzymatic activity of IdeS, or to generate a protective immune response. Typically, polypeptides with more than about 50%, 55% or 65% identity preferably at least 80% or at least 90% and particularly preferably at least 95%, at least 97% or at least 99% identity, with the amino acid sequence of SEQ ID NO:1 are considered variants of the protein. Such variants may include allelic variants and the deletion, modification or addition of single amino acids or groups of amino acids within the protein sequence, as long as the peptide maintains a basic functionality of IdeS.

The inventors have also found that it is possible to provide mutants of IdeS, in which mutation in the catalytic domain removes the cysteine protease activity of the protein. Such a mutant may comprise replacement or deletion of the catalytic cysteine residue at position 94 (C94) of IdeS. For example, cysteine may be replaced with glycine. The utility of such variants is described in more detail below. The invention also relates to variants of fragments of such a mutated IdeS, but which maintain other functions of IdeS, such as the ability to generate an immune response or bind to IgG Amino acid substitutions may be made, for example from 1, 2 or 3 to 10, 20 or 30 substitutions. The modified polypeptide generally retains activity as an IgG-specific cysteine protease. Conservative substitutions may be made, for example according to the following Table. Amino acids in the same block in the second column and preferably in the same line in the third column may be substituted for each other.

| ALIPHATIC | Non-polar | G A P |
| --- | --- | --- |
| | | I L V |
| | Polar-uncharged | C S T M |
| | | N Q |
| | Polar-charged | D E |
| | | K R |
| AROMATIC | | H F W Y |

Preferably the polypeptides comprise a cysteine residue and a histidine residue at a spacing typically found in cysteine proteases. For example, in SEQ ID NO: 1, these residues are found at a spacing of about 130aa, as is typically found in cysteine proteases.

Shorter polypeptide sequences or fragments are within the scope of the invention. For example, a peptide of at least 20 amino acids or up to 50, 60, 70, 80, 100, 150 or 200 amino acids in length is considered to fall within the scope of the invention as long as it demonstrates a basic functionality of IdeS. In particular, but not exclusively, this aspect of the invention encompasses the situation when the protein is a fragment of the complete protein sequence and may represent an IgG-binding region or an epitope. Such fragments may not retain IgG cysteine protease activity.

Polypeptides of the invention may also be chemically modified, e.g. post-translationally modified. For example, they may be glycosylated or comprise modified amino acid residues. They may be modified by the addition of histidine residues to assist their purification or by the addition of a signal sequence to promote insertion into the cell membrane. It may be desirable to provide the peptides or proteins in a form suitable for attachment to a solid support. The proteins or peptides may thus be modified to enhance their binding to a solid support for example by the addition of a cystine residue. Such modified polypeptides fall within the scope of the term "polypeptide" of the invention.

Typically, polypeptides for use in accordance with the invention display immunoglobulin cysteine protease activity, and in particular IgG cysteine protease activity. Preferably, the polypeptide cleaves IgG in the hinge region and more particularly in the hinge region of the heavy chain. Preferably, cleavage results in production of Fc and Fab fragments of IgG. Preferably the activity is specific for IgG. The cysteine protease activity may be determined by means of a suitable assay. For example, a test polypeptide may be incubated with IgG at a suitable temperature such as 37° C. The starting materials and the reaction products may then be analysed by SDS PAGE to determine whether the desired IgG cleavage product is present. Typically this cleavage product is a 31 kDa fragment. Typically there is no further degradation of IgG after this first cleavage. The cleavage product may be subjected to N-terminal sequencing to verify that cleavage has occurred in the hinge region of IgG. Preferably the N-terminal sequence comprises the sequence in SEQ ID NO:8.

The cysteine protease activity of the polypeptides can be further characterised by inhibition studies. Preferably, the activity is inhibited by the peptide derivate Z-LVG-CHN$_2$ and/or by iodoacetic acid both of which are protease inhibitors. However, the activity is generally not inhibited by E64.

The cysteine protease activity of the polypeptides is generally IgG-specific in that the polypeptides may not degrade the other classes of Ig, namely IgM, IgA, IgD and IgE, when incubated with these immunoglobulins under conditions that permit cleavage of IgG. In preferred embodiments the polypeptide has the ability to cleave human, rabbit or goat IgG, and preferably does not have the ability to cleave murine IgG.

The invention also relates to mutant IdeS, in which the catalytic cysteine protease activity has been reduced or lost. The absence of cysteine protease activity may be assayed as described for non-mutant IdeS. Such mutants may retain the ability to bind IgG. Binding of IgG can be assayed by binding studies, for example immobilising IdeS, and contacting said immobilised IdeS with IgG, and monitoring for the presence of any bound IgG. Such a mutant may display no cysteine protease activity or reduced cysteine protease activity compared to a polypeptide not so modified.

According to one aspect of the invention, the polypeptides provided are capable of generating an immune response, preferably a protective immune response to S. pyogenes in an individual. These polypeptides are useful for inclusion in vaccines targeting S. pyogenes infection. In preferred embodiments, the polypeptide generates antibodies which have the ability to block the enzymatic activity of IdeS. This activity may be monitored, for example as described for IdeS activity, in which IdeS or a variant thereof retaining IgG cysteine protease activity is incubated with IgG in the presence of the generated antibody. Cleavage of IgG by IdeS can be monitored as before. The polypeptides can also be used to generate antibodies which can be used in the diagnosis or treatment by immunotherapy of S. pyogenes infection. Such polypeptides may comprise an epitope of the IdeS polypeptide and may not otherwise demonstrate the IgG cysteine protease activity. Preferably the polypeptides are fragments. For example, the fragments may be at least 6 amino acids in length, preferably at least 10, such as at least 12 or 15 or up to 20, 30 or 40 amino acids. Longer fragments such as up to 60 or 150 aa in length may also be used.

A peptide for generating an immune response may be identified by immunisation studies. For example, a candidate peptide may be administered to an animal and subsequently the antibody or T-cell response generated which is specific for the peptide may be determined. Antiserum generated following administration of a peptide to an animal may be evaluated for the ability to bind the peptide or to bind IdeS. Subsequently the animal may be challenged with S. pyogenes to evaluate whether a protective immune response has been generated.

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 50%, e.g. more than 80%, 90%, 95% or 99%, by weight of the polypeptide in the preparation is a polypeptide of the invention.

A protein or peptide of the invention may be labelled with a revealing label. The revealing label may be any suitable label which allows the protein or peptide to be detected. Suitable labels include radioisotopes such as $^{125}$I, $^{35}$S or enzymes, antibodies, polynucleotides and linkers such as biotin. Labelled polypeptides of the invention may be used in diagnostic procedures such as immunoassays. In such assays it may be preferred to provide the peptides attached to a solid support, for example, the surface of an immunoassay well or dipstick. The present invention also relates to such labelled and/or immobilized polypeptides packaged in the form of a kit in a container. The kit may optionally contain other suitable reagent(s), control(s) or instructions and the like.

Polypeptides for use in the present invention may be isolated from suitable IdeS expressing strains of S. pyogenes. Suitable strains may be identified by a number of techniques. For example, S. pyogenes strains may initially be tested for the presence an ideS gene. Polynucleotide primers or probes may be designed based on for example, SEQ ID Nos 1, 2 or 3. Suitable primers are set out in SEQ ID NOs 4, 5, 6 and 7. The presence of the ides gene can then be verified by PCR using the primers or by hybridisation of the probes to genomic DNA of the S. pyogenes strain.

S. pyogenes strains expressing active IdeS can be identified by assaying for IgG cysteine protease activity in the culture supernatant. Preferably inhibitor E64 is added to the supernatant to inhibit any SpeB cysteine protease activity. The present inventors have shown that at least five strains tested express active IdeS: strains AP1, AP12, AP255, KTL3 and SF370. Preferably the expressing strain is selected from AP1, AP12 and AP55.

Isolation and purification of IdeS from an expressing S. pyogenes culture is typically on the basis of IgG cysteine protease activity. Preferably the purification method involves an ammonium sulphate precipitation step and an ion exchange chromatography step. According to one method, the culture medium is fractionated by adding increasing amounts of ammonium sulphate. The amounts of ammonium sulphate may be 10 to 80%. Preferably the culture medium is fractionated with 50% ammonium sulphate, and the resulting supernatant is further precipitated with 70% ammonium sulphate. Pelleted proteins may then be subjected to ion exchange chromatography, for example by FPLC on a Mono Q column. Eluted fractions may be assayed for IgG cysteine protease activity and peak activity factions may be pooled. Fractions may be analysed by SDS PAGE. For example, an N-terminal sequence can be obtained from the SDS PAGE protein band. Fractions may be stored at −20° C.

Polypeptides for use in the invention may also be prepared as fragments of such isolated proteins. Further, the proteins and peptides of the invention may also be made synthetically or by recombinant means as discussed below.

The amino acid sequence of proteins and polypeptides of the invention may be modified to include non-naturally occurring amino acids or to increase the stability of the compound. When the proteins or peptides are produced by synthetic means, such amino acids may be introduced during production. The proteins or peptides may also be modified following either synthetic or recombinant production.

The proteins or peptides of the invention may also be produced using D-amino acids. In such cases the amino acids will be linked in reverse sequence in the C to N orientation. This is conventional in the art for producing such proteins or peptides.

A number of side chain modifications are known in the art and may be made to the side chains of the proteins or peptides of the present invention. Such modifications include, for example, modifications of amino acids by reductive alkylation by reaction with an aldehyde followed by reduction with NaBH$_4$, amidination with methylacetimidate or acylation with acetic anhydride.

The invention also relates to polynucleotides encoding the above polypeptides, and their use in medicine. In particular the invention relates to polynucleotides comprising or consisting of (a) the coding sequence of SEQ ID NO:3 or a complementary sequence thereto; (b) sequence which hybridises under stringent conditions to the sequences defined in (a); (c) sequence which is degenerate as a result of the genetic code to sequence as defined in (a) or (b); (d) sequence having at least 60% identity to sequences defined in (a) (b) or (c); and (e) fragments of the above sequences.

Typically the polynucleotide is DNA. However, the invention may comprise RNA polynucleotides. The polynucleotides may be single or double stranded, and may include within them synthetic or modified nucleotides.

A polynucleotide of the invention can hybridize to the coding sequence or the complement of the coding sequence of SEQ ID NO: 3 at a level significantly above background. Background hybridization may occur, for example, because of other DNAs present in a DNA library. The signal level generated by the interaction between a polynucleotide of the invention and the coding sequence or complement of the coding sequence of SEQ ID NO: 3 is typically at least 10 fold, preferably at least 100 fold, as intense as interactions between other polynucleotides and the coding sequence of SEQ ID NO: 3. The intensity of interaction may be measured, for example, by radiolabelling the probe, e.g. with $^{32}$P. Selective hybridisation may typically be achieved using conditions of medium to high stringency. However, such hybridisation may be carried out under any suitable conditions known in the art (see Sambrook et al, 1989. For example, if high stringency is required suitable conditions include from 0.1 to 0.2×SSC at 60° C. up to 65° C. If lower stringency is required suitable conditions include 2×SSC at 60° C.

The coding sequence of SEQ ID NO: 3 may be modified by nucleotide substitutions, for example from 1, 2 or 3 to 10, 25, 50 or 100 substitutions. The polynucleotide of SEQ ID NO: 3 may alternatively or additionally be modified by one or more insertions and/or deletions and/or by an extension at either or both ends. Additional sequences such as signal sequences may also be included. The modified polynucleotide generally encodes a polypeptide which has IgG specific cysteine protease activity. Alternatively, a polynucleotide encodes an epitope portion of an IdeS polypeptide. Degenerate substitutions may be made and/or substitutions may be made which would result in a conservative amino acid substitution when the modified sequence is translated, for example as shown in the Table above.

A nucleotide sequence which is capable of selectively hybridizing to the complement of the DNA coding sequence of SEQ ID NO: 3 will generally have at least 60%, at least 70%, at least 80%, at least 90%, at least 95%, at least 98% or at least 99% sequence identity to the coding sequence of SEQ ID NO: 3 over a region of at least 20, preferably at least 30, for instance at least 40, at least 60, more preferably at least 100 contiguous nucleotides or most preferably over the full length of SEQ ID NO: 3.

For example the UWGCG Package provides the BESTFIT program which can be used to calculate homology (for example used on its default settings) (Devereux et al (1984) *Nucleic Acids Research* 12, p 387-395). The PILEUP and BLAST algorithms can be used to calculate homology or line up sequences (typically on their default settings), for example as described in Altschul (1993) J. Mol. Evol. 36:290-300; Altschul et al (1990) J. Mol. Biol. 215:403-10.

Software for performing BLAST analyses is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, 1990). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Nati. Acad Sci.* USA 89: 10915-10919) alignments (B) of 50, expectation (B) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Any combination of the above mentioned degrees of sequence identity and minimum sizes may be used to define polynucleotides of the invention, with the more stringent combinations (i.e. higher sequence identity over longer lengths) being preferred. Thus, for example a polynucleotide which has at least 90% sequence identity over 25, preferably over 30 nucleotides forms one aspect of the invention, as does a polynucleotide which has at least 95% sequence identity over 40 nucleotides.

Polynucleotide fragments, such as those suitable for use as probes or primers will preferably be at least 10, preferably at least 15 or at least 20, for example at least 25, at least 30 or at least 40 nucleotides in length. They will typically be up to 40, 50, 60, 70, 100 or 150 nucleotides in length. Probes and fragments can be longer than 150 nucleotides in length, for example up to 200, 300, 400, 500, 600, 700 nucleotides in length, or even up to a few nucleotides, such as five or ten nucleotides, short of the coding sequence of SEQ D NO: 3.

Polynucleotides according to the invention may be produced recombinantly, synthetically, or by any means available to those of skill in the art. They may also be cloned by standard techniques. The polynucleotides are typically provided in isolated and/or purified form.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR (polymerase chain reaction) cloning techniques. This will involve analyzing a pair of primers (e.g. of about 15-30 nucleotides) to a region of the ideS gene which it is desired to clone, bringing the primers into contact with DNA obtained from a bacterial cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector. Suitable primers are for example, those in SEQ ID Nos 4, 5, 6 or 7.

Such techniques may be used to obtain all or part of the ideS gene sequence described herein. Although in general the techniques mentioned herein are well known in the art, reference may be made in particular to Sambrook et al, Molecular Cloning: A Laboratory Manual, 1989.

The polynucleotides according to the invention have utility in production of the polypeptides according to the invention, which may take place in vitro, in vivo or ex vivo. The polynucleotides may be used as therapeutic or immunisation agents in their own right or may be involved in recombinant protein synthesis.

Polynucleotides of the invention may be used as a primer, e.g. a PCR primer, a primer for an alternative amplification reaction, a probe e.g. labelled with a revealing label by conventional means using radioactive or non-radioactive labels, or the polynucleotides may be cloned into vectors.

Polynucleotides or primers of the invention may carry a revealing label. Suitable labels include radioisotopes such as $^{32}P$ or $^{35}S$, enzyme labels, or other protein labels such as biotin. Such labels may be added to polynucleotides or primers of the invention and may be detected using techniques known per se.

Polynucleotides or primers of the invention or fragments thereof, labelled or unlabelled, may be used by a person skilled in the art in nucleic acid-based tests for detecting or sequencing ideS in a sample.

Such tests for detecting generally comprise bringing a sample containing DNA or RNA into contact with a probe comprising a polynucleotide or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which has hybridized to the probe. Alternatively, the sample nucleic acid may be immobilized on a solid support, and the amount of probe bound to such a support can be detected.

The probes of the invention may conveniently be packaged in the form of a test kit in a suitable container. In such kits the probe may be bound to a solid support where the assay formats for which the kit is designed requires such binding. The kit may also contain suitable reagents for treating the sample to be probed, hybridizing the probe to nucleic acid in the sample, control reagents, instructions, and the like.

The polynucleotides of the invention may be incorporated into a recombinant replicable vector. The vector may be used to replicate the nucleic acid in a compatible host cell. Therefore, polynucleotides of the invention may be made by introducing a polynucleotide of the invention into a replicable vector, introducing the vector into a compatible host cell and growing the host cell under conditions which bring about replication of the vector.

Preferably the vector is an expression vector comprising a nucleic acid sequence that encodes a polypeptide of the invention. Such expression vectors are routinely constructed in the art of molecular biology and may for example involve the use of plasmid DNA and appropriate initiators, promoters, enhancers and other elements, which may be necessary, and which are positioned in the correct orientation, in order to allow for protein expression. Other suitable vectors would be apparent to persons skilled in the art. By way of further example in this regard we refer to Sambrook et al. 1989.

Polynucleotides according to the invention may also be inserted into the vectors described above in an antisense orientation in order to provide for the production of antisense RNA. Anti sense RNA or other antisense polynucleotides or interfering RNA, iRNA may also be produced by synthetic means. Such antisense polynucleotides or iRNA may be used as test compounds in the assays of the invention or may be useful in a method of treatment of the human or animal body by therapy.

Preferably, a polynucleotide of the invention or for use in the invention in a vector is operably linked to a control sequence which is capable of providing for the expression of the coding sequence by the host cell, i.e. the vector is an expression vector. The term "operably linked" refers to a juxtaposition wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with a origin of replication, optionally a promoter for the expression of the said polynucleotide and optionally a regulator of the promoter. The vectors may contain one or more selectable marker genes, for example an ampicillin resistance gene in the case of a bacterial plasmid or a resistance gene for a fungal vector.

Promoters and other expression regulation signals may be selected to be compatible with the host cell for which expression is designed. For example, yeast promoters include *S. cerevisiae* GAL4 and ADH promoters, *S. pombe* nmt1 and adh promoter. Mammalian promoters include the metallothionein promoter which can be induced in response to heavy metals such as cadmium. Viral promoters such as the SV40 large T antigen promoter or adenovirus promoters may also be used. All these promoters are readily available in the art.

Mammalian promoters, such as β-actin promoters, may be used. Tissue-specific promoters are especially preferred. Viral promoters may also be used, for example the Moloney murine leukaemia virus long terminal repeat (MMLV LTR), the rous sarcoma virus (RSV) LTR promoter, the SV40 promoter, the human cytomegalovirus (CMV) IE promoter, adenovirus, HSV promoters (such as the HSV IE promoters), or IPV promoters, particularly the HPV upstream regulatory region (URR). Viral promoters are readily available in the art.

The vector may further include sequences flanking the polynucleotide giving rise to polynucleotides which comprise sequences homologous to eukaryotic genomic sequences, preferably mammalian genomic sequences, or viral genomic sequences. This will allow the introduction of the polynucleotides of the invention into the genome of eukaryotic cells or viruses by homologous recombination. In particular, a plasmid vector comprising the expression cassette flanked by viral sequences can be used to prepare a viral vector suitable for delivering the polynucleotides of the invention to a mammalian cell. Other examples of suitable viral vectors include herpes simplex viral vectors and retroviruses, including lentiviruses, adenoviruses, adeno-associated viruses and HPV viruses. Gene transfer techniques using these viruses are known to those skilled in the art. Retrovirus vectors for example may be used to stably integrate the polynucleotide giving rise to the polynucleotide into the host genome. Replication-defective adenovirus vectors by contrast remain episomal and therefore allow transient expression.

Vectors may be used in vitro, for example for the production of DNA or RNA or used to transfect or transform a host cell, for example, a mammalian host cell. The vectors may also be adapted to be used in vivo, for example in a method of gene therapy or nucleic acid immunisation.

Expression vectors may be transformed into a suitable host cell to provide for expression of a polypeptide or polypeptide fragment of the invention. The host cell, transformed or transfected with an expression vector as described above, is cultivated under conditions to allow for expression of the polypeptide or fragment, and the expressed polypeptide or fragment is recovered. Isolation and purification may be carried out as described above. Host cells will be chosen to be compatible with the vector and will preferably be bacterial. Host cells may also be cells of a non-human animal, or a plant transformed with a polynucleotide of the invention.

According to another aspect, the present invention also relates to antibodies capable of specific binding to a polypeptide of the invention. Such antibodies are for example useful in purification, isolation or screening methods or indeed as therapeutic agents in their own right.

Antibodies may be raised against specific epitopes of the polypeptides according to the invention. An antibody, or other compound, "specifically binds" to a protein when it binds with preferential or high affinity to the protein for which it is specific but does substantially bind not bind or binds with only low affinity to other proteins. A variety of protocols for competitive binding or immunoradiometric assays to determine the specific binding capability of an antibody are well known in the art (see for example Maddox et al, J. Exp. Med. 158, 1211-1226, 1993). Such immunoassays typically involve the formation of complexes between the specific protein and its antibody and the measurement of complex formation.

For the purposes of this invention, the term "antibody", unless specified to the contrary, includes fragments which bind a polypeptide of the invention. Such fragments include Fv, F(ab') and F(ab')$_2$ fragments, as well as single chain antibodies. Furthermore, the antibodies and fragment thereof may be chimeric antibodies, CDR-grafted antibodies or humanised antibodies.

Antibodies of the invention can be produced by any suitable method. Means for preparing and characterising antibodies are well known in the art, see for example Harlow and Lane (1988) "Antibodies: A Laboratory Manual", Cold Spring Harbor Laboratory Press, Cold Spring Harbor, N.Y. For example, an antibody may be produced by raising antibody in a host animal against the whole polypeptide or a fragment thereof, for example an antigenic epitope thereof, herein after the "immunogen".

A method for producing a polyclonal antibody comprises immunising a suitable host animal, for example an experimental animal, with the immunogen and isolating immunoglobulins from the animal's serum. The animal may therefore be inoculated with the immunogen, blood subsequently removed from the animal and the IgG fraction purified.

A method for producing a monoclonal antibody comprises immortalising cells which produce the desired antibody. Hybridoma cells may be produced by fusing spleen cells from an inoculated experimental animal with tumour cells (Kohler and Milstein (1975) Nature 256, 495-497). An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

Antibodies, both monoclonal and polyclonal, which are directed against polypeptides of the invention are particularly useful in diagnosis.

Antibodies may be used in a method for detecting polypeptides of the invention in a biological sample. Generally such a method comprises (a) incubating a biological sample with the antibody under conditions which allow for the formation of an antibody-antigen complex; and (b) determining whether antibody-antigen complex comprising the antibody is formed. A sample may be for example a tissue extract, blood, serum and saliva. Similarly, a polypeptide of the invention may be used to detect the presence of anti-IdeS antibodies in a sample, for example to provide an indicator of S. pyogenes infection. Preferably, a polypeptide of the invention for use in accordance with this aspect of the invention comprises a mutant polypeptide which does not have cysteine protease activity or has reduced cysteine protease activity, but maintains the ability to bind IgG.

Antibodies or polypeptides of the invention may be bound to a solid support and/or packaged into kits in a suitable container along with suitable reagents controls, instructions, etc. Antibodies or polypeptides may be linked to a revealing label and thus may be suitable for use in methods of in vivo imaging.

Antibodies, including antibody fragments are also useful in passive immunotherapy. Monoclonal antibodies in particular, may be used to raise anti-idiotype antibodies. Anti-idiotype antibodies are immunoglobulins which carry an "internal image" of the antigen of the infectious agent against which protection is desired. Techniques for raising anti-idiotype antibodies are well known in the art. These anti-idiotype antibodies may also be useful for treatment of S. pyogenes, as well as for an elucidation of the immunogenic regions of polypeptides of the invention.

The invention is also concerned with modulatory agents which modulate the IgG cysteine protease activity and/or expression of the present polypeptides, in particular, agents which inhibit the activity. The agents may bind to the polypeptides. The agents may modulate IgG binding of the polypeptides and/or cysteine protease activity. The present inventors have shown that inhibitors of IdeS include iodoacetic acid and Z-LVG-CHN$_2$ and also antibodies to IdeS.

Modulatory agents may be identified in screening methods using the present polypeptides. In general such screening methods comprise:
  (i) contacting a polynucleotide of the invention, a vector of the invention, a polypeptide of the invention or a cell of the invention and a test substance under conditions that would permit IgG cysteine protease activity in the absence of the test substance; and
  (ii) determining thereby whether the said substance modulates the activity and/or expression of the polypeptide.

Any suitable assay format may be used. Assay formats which allow high through put screening are preferred.

The assay may be carried out on a cell harbouring the polynucleotide or vector or on a cell extract comprising the polynucleotide or vector. The cells may express the polypeptide naturally or the polypeptide may be recombinantly expressed. The cell or cell extract will typically allow transcription and translation of the polynucleotide or vector in the absence of a test substance.

The assay may also be carried out using a polypeptide of the invention. The polypeptide may be in a purified preparation or for example in a culture supernatant. Most preferably such an assay would be carried out in a single well of a plastics microtitre plate so that high through-put screening may be carried out. Typically the polypeptide is incubated with a test substance in the dark at a temperature of 25 to 42° C. The enzyme reaction is commenced by addition of IgG. Reaction products may then be analysed by SDS PAGE.

In addition to the polypeptide, test substance and IgG substrate, the reaction mixture may contain a suitable buffer. A suitable buffer includes any suitable biological buffer that can provide buffering capability at a pH conducive to the reaction requirements of the enzyme. The assay of the invention may be carried out at any temperature at which the polypeptide, in the absence of inhibitor, is active. Typically the assay will be carried out in the range of from 25 to 42° C., in particular at 37° C.

Typically control assays are carried out in the absence of the test substance. The substance tested may be tested with any other polypeptide/enzyme to exclude the possibility that the substance is a general inhibitor of gene expression or enzyme activity. Control experiments may be carried out on cells which do not express the polypeptide of the invention to establish whether the desired responses are the result of inhibition or activation of the polypeptide. Preferably the assay is carried out in the presence of E64, an inhibitor of the SpeB cysteine protease, particularly where S. pyogenes cells are used in the assay.

Assays can also be carried out using constructs comprising an IdeS gene promoter operably linked to a heterologous coding sequence, to identify compounds which modulate expression of IdeS at the transcriptional level.

A promoter means a transcriptional promoter. IdeS promoters can be isolated via methods known to those skilled in the art and as described above. The term "heterologous" indicates that the coding sequence is not operably linked to the promoter in nature; the coding sequence is generally from a different organism to the promoter. The promoter may be fused directly to a coding sequence or via a linker. The linker sequence may comprise a sequence having enhancer characteristics, to boost expression levels.

Preferably the promoter is operably linked to the coding sequence of a reporter polypeptide. The reporter polypeptide may be, for example, the bacterial polypeptide β-glucuronidase (GUS), green fluoresent protein (GFP), luciferase (luc), chloramphenicol transferase (CAT) or β-galactosidase (lacZ).

Promoter:reporter gene constructs such as those described above can be incorporated into a recombinant replicable vector. The vector may be used to replicate the nucleic acid construct in a compatible host cell. The vectors may be, for example, plasmid, virus or phage vectors provided with an origin of replication. Any host cell may be used in which the promoter is functional, but typically the host cell will be a cell of the species from which the promoter derives. The promoter:reporter gene constructs of the invention may be introduced into host cells using conventional techniques.

Thus the invention provides a method for identifying a modulator of IdeS expression. Typically a promoter:reporter polypeptide construct or a cell harbouring that construct will be contacted with a test substance under conditions that would permit the expression of the reporter polypeptide in the absence of the test substance.

Any reporter polypeptide may be used, but typically GUS or GFP are used. GUS is assayed by measuring the hydrolysis of a suitable substrate, for example 5-bromo-4-chloro-3-indolyl-β-D-glucoronic acid (X-gluc) or 4-methylumbelliferyl-β-glucuronide (MUG). The hydrolysis of MUG yields a product which can be measured fluorometrically. GFP is quantified by measuring fluorescence at 590 nm after excitation at 494 nm. These methods are well known to those skilled in the art.

Test substances may also be assayed directly for binding to a polypeptide of the invention. For example, a radiolabelled test substance can be incubated with a polypeptide of the invention and binding of the test substance to the polypeptide monitored. Non-specific binding of the test substance may also be determined by carrying out a competitive binding assay. Substance that inhibit the interaction of a polypeptide of the invention with IgG may also be identified using a protein interaction assay such as immunoprecipitation or an ELISA based technique.

A test substance which modulates the expression or activity of a polypeptide of the invention may do so by binding directly to the relevant gene promoter, thus inhibiting or activating transcription of the gene. Inhibition may occur by preventing the initiation or completion of transcription. Activation may occur, for example by increasing the affinity of the transcription complex for the promoter. Alternatively a modulator may bind to a protein which is associated with the promoter and is required for transcription.

A substance which modulates the activity of the polypeptide may do so by binding to the enzyme. Such binding may result in activation or inhibition of the protein. Inhibition may occur, for example, if the modulator resembles the substrate and binds at the active site of the enzyme. The IgG is thus prevented from binding to the same active site and the rate of catalysis is reduced by reducing the proportion of enzyme molecules bound to substrate. A modulator which inhibits activity may do so by binding to the substrate.

Suitable test substances which can be tested in the above assays include combinatorial libraries, defined chemical entities and compounds, peptide and peptide mimetics, oligonucleotides and natural product libraries, such as display (e.g. phage display libraries) and antibody products.

Typically, organic molecules will be screened, preferably small organic molecules which have a molecular weight of from 50 to 2500 daltons. Candidate products can be biomolecules including, saccharides, fatty acids, steroids, purines, pyrimidines, derivatives, structural analogs or combinations thereof. Candidate agents are obtained from a wide variety of sources including libraries of synthetic or natural compounds. Known pharmacological agents may be subjected to directed or random chemical modifications, such as acylation, alkylation, esterification, amidification, etc. to produce structural analogs.

Test substances may be used in an initial screen of, for example, 10 substances per reaction, and the substances of these batches which show inhibition or activation tested individually. Test substances may be used at a concentration of from 1 nM to 1000 μM, preferably from 1 μM to 100 μM, more preferably from 1 μM to 10 μM. Preferably, the activity of a test substance is compared to the activity shown by a known activator or inhibitor.

A modulator of expression and/or activity of the present polypeptide is one which produces a measurable reduction or increase in expression and/or activity in assays such as those described above. Thus, modulators may be inhibitors or activators of expression and/or activity.

Preferred inhibitors are those which inhibit expression and/or activity by at least 10%, at least 20%, at least 30%, at least 40% at least 50, at least 60%, at least 70%, at least 80%, at least 90%, at least 95% or at least 99% at a concentration of the inhibitor of 1 µg ml$^{-1}$, 10 µg ml$^{-1}$, 100 µg ml$^{-1}$, 500 µg ml$^{-1}$, 1 mg ml$^{-1}$, 10 mg ml$^{-1}$, 100 mg ml$^{-1}$.

Preferred activitors are those which activate expression and/or activity by at least 10%, at least 25%, at least 50%, at least 100%, at least, 200%, at least 500% or at least 1000% at a concentration of the activator 1 µg ml$^{-1}$, 10 µg ml$^{-1}$, 100 µg ml$^{-1}$, 500 µg ml$^{-1}$, 1 mg ml$^{-1}$, 10 mg ml$^{-1}$, 100 mg ml$^{-1}$.

The percentage inhibition or activation represents the percentage decrease or increase in expression/activity in a comparison of assays in the presence and absence of the test substance. Any combination of the above mentioned degrees of percentage inhibition or activation and concentration of inhibitor or activator may be used to define an inhibitor or activator of the invention, with greater inhibition or activation at lower concentrations being preferred.

The present invention provides the polypeptides, polynucleotides, antibodies and agents described above for use in therapy or prophylexis. In particular, the polypeptides, polynucleotides, antibodies and agents are useful for the treatment of S. pyogenes infection of a human or animal. Treatment may be therapeutic or prophylactic.

Preferably, the infecting S. pyogenes strain is an IdeS-expressing strain. Such strains may be identified as described above. Typically the strain is of the M1, M12 or M55 serotype. Examples of suitable strains include AP1, AP12, AP55, KTL3 and SF370. In a preferred embodiment, the strain is of M1 serotype, such as AP1.

Conditions which may be usefully targeted include those associated with acute infection and also sequelae following acute infection. Examples include but are not limited to impetigo, pharyngitis, septicaemia, necrotizing fasciitis, streptococcal toxic-shock syndrome, acute rheumatic fever and post-streptoccal glomerulonephritis.

Preferably the individual to be treated is human.

The invention additionally provides pharmaceutical compositions comprising the polypeptides, polynucleotides, antibodies or agents of the invention and a pharmaceutically acceptable carrier or diluent.

Formulation with standard pharmaceutically acceptable carriers and/or excipients may be carried out using routine methods in the pharmaceutical art. For example, an active substance may be dissolved in physiological saline or water for injections. The exact nature of a formulation will depend upon several factors including the particular substance to be administered and the desired route of administration. Suitable types of formulation are fully described in Remington's Pharmaceutical Sciences, Mack Publishing Company, Eastern Pennsylvania, 17$^{th}$ Ed. 1985, the disclosure of which is included herein of its entirety by way of reference.

The substances may be administered by enteral or parenteral routes such as via oral, buccal, anal, pulmonary, intravenous, intra-arterial, intramuscular, intraperitoneal, topical or other appropriate administration routes.

The polypeptides and polynucleotides of the invention are useful for prophylactic treatment of individuals. Typically the polypeptide or polynucleotide used represents or encodes an epitope of IdeS. In general, the polypeptide or polynucleotide is capable of generating an immune, in particular a protective immune response in the individual to be treated. Preferably antibodies that have the ability to block the IgG enzymatic activity of IdeS are generated. Such polypeptides and polynucleotides may be identified by the methods described above.

Generally for such uses, the polypeptides, polynucleotides are incorporated in vaccine compositions.

Vaccines may be prepared from one or more of the proteins or peptides of the invention and a physiologically acceptable carrier or diluent. Typically, such vaccines are prepared as injectables, either as liquid solutions or suspensions; solid forms suitable for solution in, or suspension in, liquid prior to injection may also be prepared. The preparation may also be emulsified, or the protein encapsulated in a liposome. The active immunogenic ingredient may be mixed with an excipient which is pharmaceutically acceptable and compatible with the active ingredient. Suitable excipients are, for example, water, saline, dextrose, glycerol, ethanol, of the like and combinations thereof.

In addition, if desired, the vaccine may contain minor amounts of auxiliary substances such as wetting or emulsifying agents, pH buffering agents, and/or adjuvants which enhance the effectiveness of the vaccine. Examples of adjuvants which may be effective include but are not limited to: aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (CGP 19835A, referred to as MTP-PE), and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against an immunogenic polypeptide containing an IdeS antigenic sequence resulting from administration of this polypeptide in vaccines which are also comprised of the various adjuvants.

The vaccines are conventionally administered parentally, by injection, for example, either subcutaneously or intramuscularly. Additional formulations which are suitable for other modes of administration include suppositories, oral formulations and formulations for transdermal administration. For suppositories, traditional binders and carriers may include, for example, polyalkylene glycols or triglycerides; such suppositories may be formed from mixtures containing the active ingredient in the range of 0.5% to 10%, preferably 1% to 2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the vaccine composition is lyophilised, the lyophilised material may be reconstituted prior to administration, e.g. a suspension. Reconstitution is preferably effected in buffer.

Capsules, tablets and pills for oral administration to a patient may be provided with an enteric coating comprising, for example, Eudragit "S", Eudragit "L", cellulose acetate, cellulose acetate phthalate or hydroxypropylmethyl cellulose.

Vaccine compositions suitable for delivery by needleless injection, for example, transdermally, may also be used.

The proteins or peptides of the invention may be formulated into the vaccine as neutral or salt forms. Pharmaceutically acceptable salts include the acid addition salt (formed with free amino groups of the peptide) and which are formed with inorganic acids such as, for example, hydrochloric or phosphoric acids, or such organic acids such as acetic, oxalic, tartaric and maleic. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine and procaine.

The vaccines are administered in a manner compatible with the dosage formulation and in such amount will be prophylactically and/or therapeutically effective. The quantity to be administered, which is generally in the range of 5 μg to 100 mg, preferably 250 μg to 10 mg of antigen per dose, depends on the subject to be treated, capacity of the subject's immune system to synthesize antibodies, and the degree of protection desired. Precise amounts of active ingredient required to be administered may depend on the judgement of the practitioner and may be peculiar to each subject.

The vaccine may be given in a single dose schedule, or preferably in a multiple dose schedule. A multiple does schedule is one in which a primary course of vaccination may be 1-10 separate doses, followed by other doses given at subsequent time intervals required to maintain and or reinforce the immune response, for example at 1 to 4 months for a second dose, and if needed, a subsequent dose(s) after several months. The dosage regimen will also, at least in part, be determined by the need of the individual and be dependent upon the judgement of the practitioner.

The nucleotide sequences of the invention and expression vectors can also be used as vaccine formulations as outlined above. Preferably, the nucleic acid, such as RNA or DNA, in particular DNA, is provided in the form of an expression vector, which may be expressed in the cells of the individual to be treated. The vaccines may comprise naked nucleotide sequences or be in combination with cationic lipids, polymers or targeting systems. The vaccines may be delivered by any available technique. For example, the nucleic acid may be introduced by needle injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to mucosal surfaces for example by intranasal, oral, intravaginal or intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably to 1 pg to 10 μg nucleic acid for particle mediated gene delivery and 10 μg to 1 mg for other routes.

Inhibitory agents, for example, identified according to the above screening methods may also be useful in preventing or treating infection-associated conditions. These agents may be formulated with standard pharmaceutically acceptable carriers and/or excipients using routine methods.

The antibodies and agents of the invention may be useful for therapeutic treatment of S. pyogenes infections.

Antibodies of the invention, both polyclonal and monoclonal, which are neutralising, are useful in passive immunotherapy. Monoclonal antibodies in particular, may be used to raise anti-idiotype antibodies as above. These anti-idiotype antibodies may also be useful for treatment of S. pyogenes, as well as for an elucidation of the immunogenic regions of polypeptides of the invention. Antibody fragments, for example, Fab fragments, may also be useful in immunotherapy of S. pyogenes infection.

The antibodies of the invention may be formulated with a pharmaceutically acceptable carrier and delivered in the same way as set out for the vaccine compositions. Preferably the antibody is administered in an amount effective to ameliorate S. pyogenes infection in the individual.

Inhibitors of IdeS activity, for example those identified by the above screening methods may be useful for therapeutic treatment of S. pyogenes infections. These agents may be formulated with standard pharmaceutically acceptable carriers and/or excipients using routine methods and delivered in the same way as set out for the vaccine compositions. The inhibitor is administered to an individual in a therapeutically effective amount. The dose of an inhibitor may be determined according to various parameters, especially according to the substance used; the age, weight and condition of the patient to be treated; the route of administration; and the required regimen. A physician will be able to determine the required route of administration and dosage for any particular patient.

In one aspect, an S. pyogenes infection may be treated by administration of both an antibody and an inhibitory agent. The antibody and the agent may be administered simultaneously, separately, or sequentially. Accordingly the invention also relates to products in which both antibody and agent are supplied for use in such a treatment regimen.

The invention is also concerned with the diagnosis of S. pyogenes infection in an individual, preferably a human. The polypeptides and antibodies of the invention may be used for such diagnosis. The polypeptides may be used to detect antibodies specific to the polypeptides in the individual or vice versa, thus determining infection. Polypeptides suitable for use in diagnosis are those which retain specific antibody binding capability. For example, such polypeptides typically comprise an epitope of IdeS. Suitable polypeptides can be identified by the methods described above. Antibodies for use in diagnosis may be identified and produced by the methods described above.

The diagnostic method may be practised in vitro or in vivo. Preferably the method is carried out in vitro using a sample taken from the individual to be tested for S. pyogenes infection. A sample may be for example a tissue extract, blood, serum or saliva. Generally, the method may involve (i) contacting a biological sample taken from the individual with a polypeptide or antibody of the invention under conditions that allow for the formation of an antibody-polypeptide complex; and (ii) determining whether antibody-polypeptide complex is formed.

Typically the polypeptides or antibodies for use in testing are suitably labelled. Suitable label and detection systems are known in the art. The polypeptides or antibodies may be bound to a solid support and/or packaged into kits in a suitable container along with suitable reagents, controls, instructions, etc. Antibodies may also be linked to a revealing label and thus may be suitable for use in methods of in vitro imaging.

In a further aspect, the present polypeptides may provide useful tools for biotechnology. For example, the polypeptides may be used for specific in vitro cleavage of IgG, in particular human IgG. In such a method, the polypeptide may be incubated with the sample containing IgG under conditions which permit the specific cysteine protease activity to occur. Specific cleavage can be verified, and the cleavage products isolated using the methods described above. The method of the invention can be used in particular to generate Fc and Fab fragments. The polypeptides may be used to cleave IgG in a sample, for example in a method to remove IgG from a sample. Such methods may be used to assist in removing immunoglobulin from a sample, or to remove IgG in the purification of other immunoglobulin.

Modified polypeptides of the invention which no longer have cysteine protease activity may be used to bind and isolate or purify IgG. For example, such polypeptide may be bound to a solid support and a sample containing IgG contacted with the support under conditions which allow IgG to bind to the polypeptide. Such a method may also be used to remove IgG from a sample, the remainder of the sample, free of IgG being collected for subsequent use or analysis. IgG may subsequently be desorbed from the solid support if required.

The polypeptides may also be used to detect IgG in a sample. In general such a detection method involves incubating the polypeptide with the sample under conditions which permit IgG-specific binding and cleavage. The presence of IgG can be verified by detection of the specific IgG cleavage products as above.

EXAMPLES

Materials and Methods

Unless indicated otherwise, the methods used are standard biochemistry and molecular biology techniques. Examples of suitable methodology textbooks include Sambrook et al., Molecular Cloning, A Laboratory Manual (1989) and Ausubel et al., Current Protocols in Molecular Biology (1995), John Wiley and Sons, Inc.

Bacterial Strains and Growth Conditions

S. pyogenes strains used in this study are listed in Table I.

| Strain | M-serotype | Reference or source | IgG cleavage (in the presence of E64) | PCR product |
|---|---|---|---|---|
| SF370 | 1 | (Suvorov and Feretti, 1996; Ferretti et al., 2001) | (+/−) | + |
| AP1 | 1 | WHO Prague collection[a] | + | + |
| AL1 | 1 | speB mutant of AP1 (Collin and Olsén, 2001a) | + | nd[d] |
| BMJ71 | 1 | mga mutant of AP1 (Kihlberg et al., 1995) | + | nd |
| KTL3 | 1 | Finnish institute for health | (+) | + |
| AP4 | 4 | WHO Prague collection | − | + |
| M5 | 5 | Sequencing in progess[b] | − | + |
| AP6 | 6 | WHO Prague collection | − | + |
| AP12 | 12 | WHO Prague collection | + | + |
| AP49 | 49 | WHO Prague collection | − | + |
| AP53 | 53 | WHO Prague collection | − | + |
| AP55 | 55 | WHO Prague collection | + | + |
| AP57 | 57 | WHO Prague collection | − | + |

Streptococci were routinely grown in Todd Hewitt broth (TH) (Difco) at 37° C. in 5% $CO_2$. Strains BMJ71 and AL1 were grown in the presence of 10 μg/ml tetracycline or 150 μg/ml kanamycin, respectively. In some cases bacteria were grown in the presence of the cysteine proteinase inhibitor trans-epoxysuccinyl-L-leucylamido-(4-Guanidino) butane (E64) (Sigma).

SDS-PAGE Analysis and N-Terminal Sequence Determination

Proteins of S. pyogenes growth media were precipitated with trichloroacetic acid (final concentration 5%), washed twice with 1 ml acetone, and resuspended in sample buffer. Proteins were separated by 12% SDS-PAGE (all SDS-PAGEs in this work were performed under reducing conditions) and stained with Coomassie Blue. For N-terminal amino acid sequence analysis proteins were separated by 10% SDS-PAGE electrophoresis and blotted onto a PVDF membrane using 10 mM CAPS buffer, 10% methanol. Proteins were visualized in 0.1% Coomassie Blue R-250, 50% methanol.

After destaining in 50% methanol, membranes were dried, protein bands cut out with a scalpel and stored at −20° C. until sequencing. Sequencing was performed at Eurosequence Company (Groningen, The Netherlands).

Purification of IdeS

IdeS was purified by growing bacteria to an $OD_{620}$ of ~0.4 and fractionating the culture supernatant with 50% ammonium sulfate. The resulting precipitate was discarded and ammonium sulfate was added to the remaining supernatant to a final concentration of 70%. The second precipitate was resuspended in 1/100 of the starting volume with 20 nM Tris-HCl, pH 8.0, and dialyzed against the same buffer. The material was further fractionated by FPLC on a Mono Q column (Pharmacia). Proteins were eluted by a linear NaCl gradient, and a peak eluted at 0.1 M NaCl was found to contain the IdeS activity. Corresponding fractions were collected, analyzed by SDS-PAGE, and saved at −20° C. until use.

IdeS Activity Assays

For standard IdeS activity assays, bacteria cultures were grown to $OD_{620}$=0.4. Bacteria were pelleted by centrifugation and supernatants were sterile-filtered through a 0.22 μm membrane (Millipore) prior to use. For activity assays, 254 μl of supernatant were mixed with 5 μl of IgG (10 mg/ml, Sigma) and the volume was adjusted with PBS to 100 μl. For screening of IdeS activity in different S. progenes strains, E64 was added to a final concentration of 40 μM. The mixtures were incubated at 37° C. for 30 min and samples were analyzed by 12% SDS-PAGE. For cleavage assays of different classes of Ig, purified IdeS (0.3 μg/ml) was incubated with 3 μg Ig for 2 h at 37° C., and analyzed by 12% SDS-PAGE analysis.

PCR Analysis of Genomic DNA for Identification of ides

To analyze the presence of the ideS gene in different streptococcal isolates, PCR template DNA was prepared by boiling S. pyogenes bacteria for 5 min in sterile water.

Cell debris was removed by centrifugation and 1 μl of the boiled lysate was used with PCR primers Ide1 (5'-CGT TAC TTC CUT TTG GAT CCA AGG-3') (SEQ ID NO:4) and Ide2 (5'-GAA ATA UCT ACT TCT CGA GCG GAA TT-3') (SEQ ID NO:5). PCR products were analyzed by agarose (1%) gel electrophoresis.

Recombinant Expression of IdeS in E. coli

For PCR amplification of ideS, template DNA was prepared by boiling S. pyogenes bacteria (strain AP1) in sterile water. The cell debris was removed by centrifugation and 5 μl of the boiled lysate was used with PCR primers Ide5X (5'-TCG GTA GAT CUT GGG ATC CTA UCA GAT AGT-3') (SEQ ID NO:6) creating a BamHI restriction site, and Ide3X (5'-CGG AAT TCT AAA TTG GTC TGA TTC CAA C-3') (SEQ ID NO:7), creating an EcoRI restriction site. A PCR fragment covering bp 79-1020 of the intact ideS gene was generated, cleaved with restriction enzymes, and cloned into the corresponding sites of plasmid pGEX-5X-3 (Amersham Pharmacia Biotech). The resulting plasmid was transformed into Escherichia coli strain BL21(DE3) pLysS, according to standard protocols (Sambrook et al., 1989). Protein expression was induced by addition of 0.1 mM isopropyl-β-D-thiogalactopyranoside (IPTG) at an $OD_{620}$ of ~0.2. Growth was continued for 3 h, and lysates were prepared by freezing bacterial pellets at −70° C., followed by resuspension in PBS. Cell debris was removed by centrifugation and 2 µl of supernatant was incubated with 5 µl of IgG (10 mg/ml) in PBS, and separated by 12% SDS-PAGE for analysis of recombinantly expressed IdeS.

Proteinase Inhibition Assays

Partially purified IdeS (0.3 µg/ml) was incubated with either 20 nM iodoacetic acid, Z-LVG-CHN$_2$ (Björck et al., 1989) at 0.4 mg/ml in 1% DMSO, or E64 (40 µM). The tubes were kept in the dark and incubated for 30 min at room temperature. As controls, IdeS was also kept in phosphate buffered saline (PBS) or in 1% DMSO, the solvent for Z-LVG-CHN$_2$. After 30 min, 5 µl of 10 mg/ml IgG (Sigma) were added, and the volume was adjusted to 100 µl with PBS. Incubation was continued for 60 min at 37° C. The reaction was stopped by the addition of SDS-PAGE sample buffer and samples were analyzed by 12% SDS-PAGE.

Cell Culture and Infection of Eukaryotic Cells

The murine macrophage-like cell line RAW 264.7 was cultured in RPMI 1640 medium (Life Technologies), supplemented with 10% FCS, and antibiotics (100 units/ml$^{-1}$ penicillin; 100 µg ml$^{-1}$ streptomycin), at 5% CO$_2$ with 100% relative humidity.

To study phagocytic killing, S. pyogenes strain AP1 was grown overnight at 37° C. AP1 bacteria were incubated with either immune or non-immune plasma, washed and treated with IdeS or a buffer control, for 2 h at 37° C. Subsequently, bacteria were washed and diluted in antibiotic-free cell culture medium prior to infection. Cell lines were carefully washed in antibiotic-free cell culture medium and bacteria were added (0.1-1 bacteria/cell) to confluent RAW264.7 cells. Infections were synchronized by gentle centrifugation at 400 g for 3 min by incubation at 37° C. Ten minutes after infection, the cell cultures were carefully washed in antibiotic-free medium to remove non-adherent bacteria (time 0 h). Control cells were lysed in ice-cold lysis buffer (0.1% Tween), diluted, and spread onto TH plates. Parallel cell cultures were incubated at 37° C. for 1 h. Subsequently, growth media was removed and cells were lysed and treated as described above. For analysis of bacterial survival the number of surviving bacteria after 1 h was divided by the number of adherent bacteria at time 0 h.

Results

S. pyogenes Secretes an IgG-Cleaving Enzyme Distinct from SpeB, the Classical Streptococcal Cysteine Proteinase The proteolytic activity of extracellular enzymes of S. pyogenes strain AP1, was analyzed by growing AP1 bacteria in Todd Hewitt (TH) medium supplemented with 10% human plasma. Following growth to stationary phase, bacteria were removed by centrifugation and the supernatant was subjected to SDS-PAGE (all SDS-PAGE's in this work were performed under reducing conditions). The band pattern was compared to the pattern of human plasma proteins that had not been in contact with bacteria (data not shown). The bacterial supernatant contained a protein band of approximately 31 kDa, which was absent in the plasma control. The N-terminal sequence of this protein was determined to GPSVFLFP (SEQ ID NO:8), which corresponds to amino acids 237-244 of the hinge region of human IgG$_1$ (FIG. 1). Recent work has shown that the streptococcal cysteine proteinase, SpeB, cleaves IgG at this site. However, most strains of S. pyogenes, including AP1, do not express the speB gene in TH medium. Moreover, the proteolytic activity of SpeB is efficiently blocked by the specific cysteine proteinase inhibitor E64, but E64 did not inhibit the cleavage of IgG when added to the AP1 growth medium, as evidenced by the continued generation of the 31 kDa IgG cleavage product (data not shown). In addition, growth medium from the isogenic SpeB deficient mutant strain AL1, also contained IgG-cleaving activity. Taken together, these data demonstrate that SpeB is not responsible for the cleavage of IgG in TH medium.

The streptococcal strain AP1 studied here, expresses a surface-associated C5a peptidase, and the IgGFc binding proteins, H and M1. The genes encoding these surface proteins are controlled by the transcriptional activator Mga, and BMJ71 is an isogenic mutant of AP1, carrying a Tn916 insertion within the mga gene. The 31 kDa IgG cleavage product is also generated in growth medium of BMJ71, showing that the proteolytic activity is not under Mga control.

Figure 2:
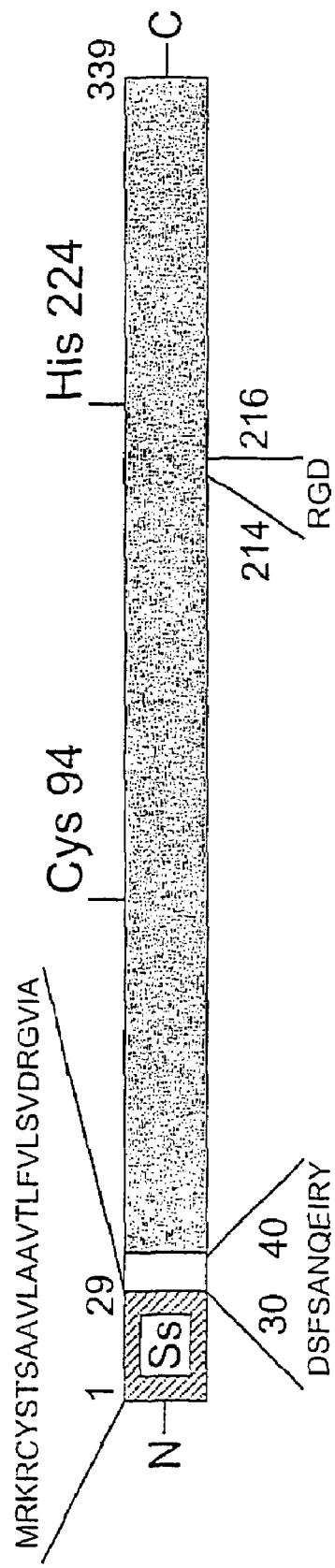
FIG. 2 shows a schematic representation of an open reading frame (ORF) encoding IdeS isolated from *S. pyogenes* AP1, including a putative signal sequence and RGD motif.

Purification and Sequence Characteristics of IdeS, a Novel Proteinase of S. pyogenes As the IgG proteolytic activity was found in the growth medium of strain AP1 we fractionated culture medium proteins after bacterial growth by adding increasing amounts of ammonium sulfate (10 to 80%). These initial experiments revealed that precipitates of 60 to 70% ammonium sulfate contained most of the IgG-cleaving activity. For purification, the growth medium was fractionated with 50% ammonium sulfate, the resulting pellet was discarded and the ammonium sulfate concentration in the supernatant was adjusted to 70%. Proteins pelleted by this second precipitation were subjected to ion-exchange chromatography and peak fractions were tested for enzymatic activity. Maximum IgG-cleaving activity was eluted at 0.1 M NaCl and the corresponding fractions contained a major band of approximately 34 kDa as judged by SDS-PAGE. This protein band was excised and subjected to N-terminal sequence analysis. The sequence obtained, DSFSANQEIRY (SEQ ID NO:9), was used to search the Streptococcal Genome Sequencing Project (SGSP) database. A perfect match was found in an open reading frame of 339 amino acids designated SPy0861. The obtained N-terminal sequence corresponds to amino acids 30-40 (FIG. 2) and was preceded by a potential signal sequence of 29 amino acids as predicted by the SignalP algorithm. The protein does not contain a cell wall attachment signal (LPXTGX) (SEQ ID NO: 10), a common feature of cell wall-anchored proteins of S. pyogenes, and the predicted size of the protein, without the potential signal sequence, is 34.9 kDa, which is in accordance with the size of the purified protein estimated by SDS-PAGE. Apart from the putative signal sequence, the protein has an RGD motif at amino acids 214-216 (FIG. 2). This motif is important for ligand recognition by integrins, and a variety of bacterial and viral pathogens have been shown to bind to host cell integrins. The full-length putative protein sequence was used in a similarity search against the DDBJ/EMBL/GenBank database using a BLASTp algorithm. This search revealed no similarities to any prokaryotic protein and a weak similarity (24% identity in a region of 204 amino acid residues) to human MAC-1 integrin alpha M precursor (Arnaout et al., 1988). Due to the absence of any previously reported function, and based on the enzymatic activity against human IgG, the protein was denoted IdeS, for Immunoglobulin degrading enzyme of Streptococcus pyogenes.

To further confirm that the identified IdeS protein has IgG cleaving activity, the ideS gene was cloned in plasmid pGEX-5X-3 (Amersham Pharmacia Biotech) and expressed in Escherichia coli. Partially purified lysates were incubated with IgG and analyzed by SDS-PAGE. Lysates from E. coli carrying the ideS gene generated the 31 kDa IgG-derived band, whereas extracts from cells carrying only a plasmid control did not cleave IgG (data not shown).

IdeS is a Novel Cysteine Proteinase Highly Specific for IgG

We noticed that the sequence of the IdeS protein contains a single cysteine residue at position 94 (FIG. 2). Despite the lack of sequence homology to other cysteine proteinases, IdeS also has a histidine residue at a distance (His 224) from the cysteine, which is often found in other cysteine proteinases, although the enzymatic activity was not inhibited by the cysteine proteinase inhibitor E64. The peptide derivate Z-LVG-CHN$_2$, structurally based on the inhibitory reactive site of cystatin C and carrying a diazomethyl ketone group to inactivate the sulfhydryl group of the catalytic cysteine, has previously been shown to irreversibly inhibit papain and SpeB. Moreover, cysteine proteinases are also inactivated by iodoacetic acid through an irreversible modification of the catalytic sulfhydryl group. We therefore investigated whether treatment with these specific inhibitors would affect the enzymatic activity of IdeS. Analysis of IgG incubated with IdeS alone or with IdeS preincubated with inhibitors, revealed that Z-LVG-CHN$_2$ and iodoacetic acid efficiently inhibited the activity of IdeS whereas E64 had no effect on the enzyme (data not shown). The activity of IdeS, its sequence characteristics, and inhibition profile, establish IdeS as a new member of the cysteine proteinase family.

Recently the streptococcal cysteine proteinase SpeB was shown to cleave the heavy chains of all classes of human immunoglobulins; IgG, IgM, IgA, IgD, and IgE. In contrast, when human IgG, IgM, IgA, IgD, or IgE, were incubated with purified IdeS for 2 h at 37° C., only IgG was degraded (data not shown). We also analyzed the activity of IdeS against the different subclasses of IgG, and found that all were susceptible for IdeS digestion, although, when compared to the other subclasses, IgG2 was less efficiently digested (not shown). The high specificity of IdeS is further emphasized by the observation that only the 31 kDa IgG-derived band and no additional degradation products could be identified following incubation of human plasma with purified IdeS. Although it cannot be excluded that the enzyme has other substrates, these data show that IdeS has a higher degree of specificity for IgG than any previously described proteinase.

Distribution and Expression of the ideS Gene in *S. pyogenes* Strains

Figure 3:
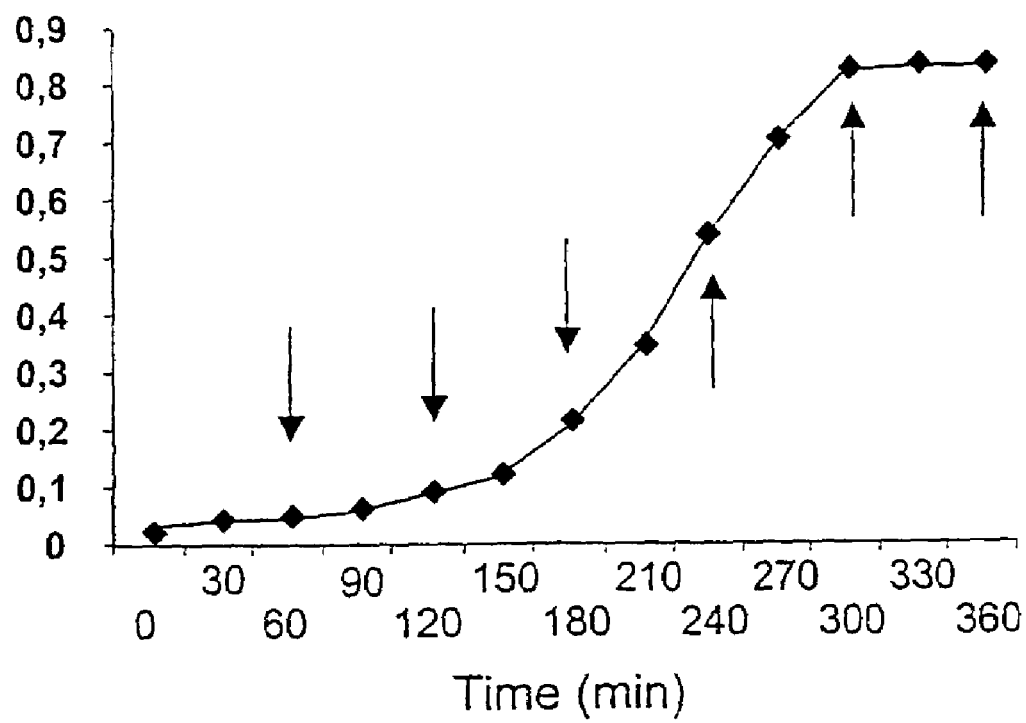
FIG. 3 shows survival factors for *S. pyogenes* bacteria in macrophage like cells, after incubation of the bacteria in immune or non-immune plasma, and with or without IdeS.
Figure 4:
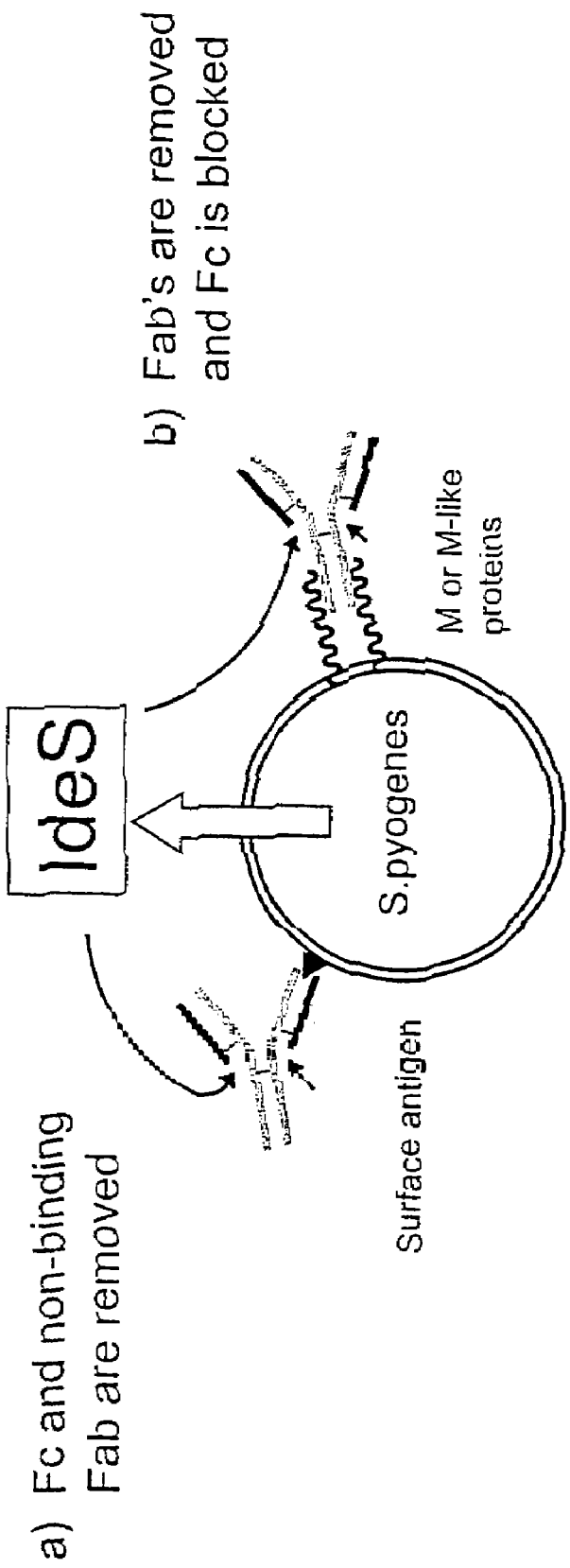
FIG. 4 shows IdeS cleavage of IgG bound to *S. pyogenes* bacterial surface.

The distribution of ideS among *S. pyogenes* strains was investigated by PCR analysis using primers designed to amplify the internal coding region of ideS. We analyzed chromosomal DNA preparations from 11 *S. pyogenes* strains of 9 different M serotypes, and were able to amplify identical PCR fragments of the expected size from all strains (Table I, data not shown). However, when analyzing the cleavage of IgG during bacterial growth in TH medium, only five of the tested strains expressed the IgG-degrading activity (AP1, KTL3, SF370, AP12, and AP55), and among these strains KTL3 and SF370 showed weak activity. Thus, although the IdeS gene seems to be present in all *S. pyogenes* isolates, expressed enzyme activity under the conditions used here, is restricted to some strains and varies even within the same M serotype (Table I). The secretion pattern of the IgG-cleaving activity during growth of strain AP1 in TH medium was also investigated. Samples were taken from the growth medium at different time points during bacterial growth, and tested for enzymatic activity against IgG. IgG-degrading activity started to appear in samples taken during early logarithmic growth phase, and the activity increased during logarithmic growth as determined from the degree of IgG cleavage. The enzymatic activity did not further increase in stationary phase supernatants but appeared to be persistent at a constant level (FIG. 3).

Fc-Mediated Phagocytosis and Killing of *S. pyogenes* is Inhibited by IdeS

Opsonizing IgG antibodies bound to surface antigens of *S. pyogenes* will expose their Fc regions to complement factor C1q and Fcγ-receptors of phagocytic cells, and thereby facilitate phagocytosis and killing of the bacteria. To test the hypothesis that IdeS by proteolytic cleavage of IgG, could interfere with this defense mechanisms, AP1 bacteria were incubated with either human immune or non-immune plasma. After incubation bacteria were washed and incubated with IdeS, or with a buffer control, followed by another washing step to remove IdeS and degradation products. Confluent RAW264.7 macrophage-like cells were then infected with these bacteria at ~0.1-1 bacteria/cell. Infections were synchronized by gentle centrifugation and cells were lysed immediately to determine the number of cfu's at time zero. In parallel infections, cell cultures were carefully washed to remove non-adherent bacteria and incubations were continued for 1 h, after which cells were lysed and the number of cfu's was determined. The ratios of cfu's at time 1 h, divided by the number of cfu's at time zero were determined as survival factors and are shown in FIG. 3. The relatively short incubation time was chosen to minimize IgG independent phagocytosis. While bacteria incubated in non-immune plasma survived contact with macrophage-like cells, the number of bacteria, which had been exposed to opsonizing immunoglobulins in immune plasma was significantly reduced ($p<0.03$) in the presence of macrophages. However, this effect was abolished when bacteria carrying opsonizing IgG were treated with IdeS prior to incubation with phagocytes (FIG. 3).

AP1 bacteria express surface proteins that bind several abundant human plasma proteins. As previously reported, following plasma absorptions, the major protein bands eluted from AP1 bacteria represent albumin, fibrinogen, and IgG heavy and light chains. The same protein pattern was obtained following absorption of non-immune or immune plasma, and in both cases IgG was cleaved by IdeS, generating IgGFc fragments, which under the reducing conditions used, give rise to the 31 kDa band (data not shown). These Fc fragments are associated with IgGFc-binding proteins, interactions that efficiently block their capacity to bind complementation factor C1q. However, as shown in FIG. 3, IdeS protects bacteria preincubated with plasma containing specific IgG antibodies. These antibodies are bound to the streptococcal surface via their antigen-binding Fab regions, suggesting that cleavage of this IgG population by IdeS will result in the removal of Fc fragments from the bacterial surface. These data demonstrate that cleavage of IgG by IdeS can occur at the bacterial surface and that IgG cleavage by IdeS increases the capacity of *S. pyogenes* to evade phagocytic cells.

The streptococcal cysteine proteinase SpeB, is well-established as a virulence determinant, and SpeB was recently shown to cleave the hinge region of IgG and to degrade the heavy chains of all human immunoglobulin classes. Therefore, the discovery of an additional extracellular cysteine proteinase in *S. pyogenes* was unexpected. However, at least under laboratory conditions, SpeB is not expressed until *S. pyogenes* reaches stationary growth phase, which makes a possible function of SpeB as an enzyme cleaving opsonizing IgG questionable. Thus, it should be important for such a proteinase to be present continuously during infection. IdeS production starts already during early logarithmic growth and continues into late stationary growth phase, which makes the enzyme more suitable to remove opsonizing IgG from the bacterial surface. Still, the actions of IdeS and SpeB could well be complementary. In fact, the identification and characterization of IdeS might explain some previous and puzzling observations. IdeS is not affected by the cysteine proteinase inhibitor E64, but is inhibited by a synthetic peptide derivative (Z-LVG-CHN$_2$), structurally based on the proteinase-binding center of cystatin C, a human cysteine proteinase inhibitor. Z-LVG-CHN$_2$ and E64 both irreversibly block the proteolytic activity of SpeB, but only Z-LVG-CHN$_2$ inhibited streptococcal growth in vitro and in vivo. However, the observation that IdeS is inhibited by Z-LVG-CHN$_2$, but not by E64, suggests that the previously observed effect of Z-LVG-CHN$_2$ on *S. pyogenes* growth and virulence, could be due to interference with both SpeB and IdeS.

In severe invasive *S. pyogenes* infections, strains of the M1 serotype are the most common, and the AP1 strain studied here and expressing IdeS, is of this serotype. Strains of serotypes M12 and M55, also producing proteolytically active IdeS under the growth conditions used, are phylogenetically closely related, and represent clinically relevant strains often connected with post-streptococcal glomerulonephritis. This correlation suggests a role for IdeS both during acute infections and in aseptic sequelae following acute *S. pyogenes* infections.

IgG is the dominant Ig class and IgGFc has important functions in complement activation and recruitment of phagocytic cells. Moreover, Fcγ receptors are expressed by all immunologically active cells. It seems that *S. pyogenes* has evolved a specific IgG-cleaving enzyme, and its specificity underlines a potential role for IdeS in preventing contact between *S. pyogenes* and phagocytes, by cleaving opsonizing IgG in the hinge region. Opsonizing IgG antibodies bind to various *S. pyogenes* surface structures via the Fab regions. However, most *S. pyogenes* strains express surface proteins of the M protein family with affinity for IgGFc. The AP1 strain studied here has two such proteins, proteins H and M1, which are structurally closed related. Large amounts of these IgGFc-binding proteins are present at the bacterial surface, and bind IgG with high affinity. As a result, AP1 bacteria surrounded by plasma or inflammatory exudate, are covered with IgG bound to these proteins through the IgGFc-binding proteins. This IgG population will be present in vast amounts compared to antigen specific IgG bound to the bacterial surface via Fab. However, the data reported here demonstrate that IdeS not only cleaves opsonizing antibodies, but also IgG bound to the surface via Fc.

Results of Further Studies

1) Substrate Specificity

IdeS exhibits high substrate specificity and has so far been found to cleave only IgG. We examined whether IdeS could have additional substrates e.g. eukaryotic plasma proteins. An extensive search for additional substrates and natural occurring inhibitors was performed.

i) Species Restrictions

IdeS was found to cleave human, rabbit and goat IgG, but not murine IgG, although the primary amino acid sequences at the cleavage site are conserved between the species.

ii) Cleavage or Other Human Proteins

No cleavage products could be detected when IdeS was incubated with whole human plasma or with fibrinogen, fibronectin, albumin, transferrin, lactoferrin, laminin, H-kininogen, α 1-antitrypsin, aprotinin, cystatin D or cystatin C.

No cleavage products could be observed when cystatin C from either chicken, rat or mouse were incubated with IdeS.

iii) Activity Towards Natural and Synthetic Peptides

Incubation of IdeS with antimicrobial peptide LL-37 or a synthetic peptide homologous to amino acids 234 to 241 of human IgG did not reveal any degradation of the peptides. Neither was the synthetic peptide Z-LVG-CHN$_2$, which inhibits IdeS activity, cleaved by excess IdeS.

Thus, to date the only known substrate for IdeS is IgG. However, we found that a Fc-fragment generated by papain cleavage, including 12 amino acids of the hinge region is cleaved by IdeS, suggesting that the recognition site of IdeS on human IgG is located in the Cγ2 region of the molecule. The Cγ2-Cγ3 interphase region of IgG has been ruled out as binding site for IdeS, as streptococcal proteins H and G, both of which bind to this region, cannot inhibit IdeS activity.

2) Neutralizing Antibodies Against the Enzymatic Activity of IdeS

An extensive analysis of antibody titers against IdeS in 80 healthy blood donors and 70 patients suffering from invasive *S. pyogenes* infections was performed.

All blood donors showed detectable antibody levels against IdeS, emphasizing that IdeS is expressed iii vivo during the course of streptococcal infections. Patients with invasive *S. pyogenes* infections showed significantly higher acute phase antibody levels against IdeS (mean ELISA index increase from 0.64 in blood donors to 1.24 in patient sera; p<0.05). Several serum samples from patients recovering from streptococcal infections (pharyngitis and sepsis) show increased antibody titers against IdeS compared to acute phase titers. Antibodies in the majority of the convalescent sera analyzed, but not in all, had the ability to block the enzymatic activity of IdeS. This finding is a very strong indication for the importance of the enzymatic activity in vivo.

The invention claimed is:

1. A method of generating Fc or Fab fragments of IgG comprising:
   (i) contacting IgG with:
       a) polypeptide having the sequence of SEQ ID NO: 1, or
       b) a polypeptide having the sequence of SEQ ID NO: 1 except for 1, 2 or 3 conservative substitutions,
   wherein said polypeptide (a) and said polypeptide (b) have a cysteine residue at the position corresponding to position 65 of SEQ ID NO:1, position 65 of SEQ ID NO:1 corresponding to position 94 of SEQ ID NO:2,
   wherein IgG is contacted with said polypeptide (a) or said polypeptide (b) under conditions that permit the IgG specific cysteine protease activity of said polypeptide (a) or said polypeptide (b);
   (ii) thereby generating said fragments of IgG; and
   (iii) isolating the fragments of IgG obtained, or analysing the starting materials or reaction products to determine whether the desired product is present.

2. The method according to claim 1 wherein the IgG is human IgG.

3. A method for detecting IgG in a sample, comprising:
   (i) contacting said sample with a substantially purified polypeptide, said polypeptide:
       a) having the sequence of SEQ ID NO: 1, or
       b) having the sequence of SEQ ID NO: 1 except for 1, 2 or 3 conservative substitutions
   wherein said polypeptide (a) and said polypeptide (b) have a cysteine residue at the position corresponding to position 65 of SEQ ID NO:1, position 65 of SEQ ID NO:1 corresponding to position 94 of SEQ ID NO:2,
   wherein IgG is contacted with said polypeptide (a) or said polypeptide (b) under conditions that permit the IgG specific cysteine protease activity of said polypeptide (a) or said polypeptide (b);
   and
   (ii) monitoring for the presence of IgG specific cleavage fragments; wherein the presence of the specific cleavage fragments is indicative of IgG in the sample.

4. The method according to claim 3 wherein the IgG is human IgG.

5. The method according to claim 3 wherein the IgG specific cleavage fragments are Fc and Fab fragments.

* * * * *

SEQUENCE LISTING

```
<160> NUMBER OF SEQ ID NOS: 10

<210> SEQ ID NO 1
<211> LENGTH: 310
<212> TYPE: PRT
<213> ORGANISM: S. Pyogenes

<400> SEQUENCE: 1

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30
```

```
Phe Thr Gln Gly Glu Asp Val Phe His Ala Pro Tyr Val Ala Asn Gln
            35                  40                  45

Gly Trp Tyr Asp Ile Thr Lys Thr Phe Asn Gly Lys Asp Asp Leu Leu
 50                  55                  60

Cys Gly Ala Ala Thr Ala Gly Asn Met Leu His Trp Trp Phe Asp Gln
 65                  70                  75                  80

Asn Lys Asp Gln Ile Lys Arg Tyr Leu Glu Glu His Pro Glu Lys Gln
                 85                  90                  95

Lys Ile Asn Phe Asn Gly Glu Gln Met Phe Asp Val Lys Glu Ala Ile
                100                 105                 110

Asp Thr Lys Asn His Gln Leu Asp Ser Lys Leu Phe Glu Tyr Phe Lys
            115                 120                 125

Glu Lys Ala Phe Pro Tyr Leu Ser Thr Lys His Leu Gly Val Phe Pro
130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asp Gln Ser Lys Leu Leu
                180                 185                 190

Thr Ser Arg His Asp Phe Lys Glu Lys Asn Leu Lys Glu Ile Ser Asp
            195                 200                 205

Leu Ile Lys Lys Glu Leu Thr Glu Gly Lys Ala Leu Gly Leu Ser His
210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
                260                 265                 270

Ser Ala Gly Lys Val Ala Ile Ser Ala Lys Glu Ile Lys Glu Asp Asn
            275                 280                 285

Ile Gly Ala Gln Val Leu Gly Leu Phe Thr Leu Ser Thr Gly Gln Asp
290                 295                 300

Ser Trp Asn Gln Thr Asn
305                 310

<210> SEQ ID NO 2
<211> LENGTH: 339
<212> TYPE: PRT
<213> ORGANISM: S. Pyogenes

<400> SEQUENCE: 2

Met Arg Lys Arg Cys Tyr Ser Thr Ser Ala Ala Val Leu Ala Ala Val
 1               5                  10                  15

Thr Leu Phe Val Leu Ser Val Asp Arg Gly Val Ile Ala Asp Ser Phe
                20                  25                  30

Ser Ala Asn Gln Glu Ile Arg Tyr Ser Glu Val Thr Pro Tyr His Val
            35                  40                  45

Thr Ser Val Trp Thr Lys Gly Val Thr Pro Pro Ala Asn Phe Thr Gln
 50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95
```

```
Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
            115                 120                 125

Phe Asn Gly Glu Gln Met Phe Asp Val Lys Glu Ala Ile Asp Thr Lys
        130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn

<210> SEQ ID NO 3
<211> LENGTH: 1020
<212> TYPE: DNA
<213> ORGANISM: S. Pyogenes

<400> SEQUENCE: 3
atgagaaaaa gatgctattc aacttcagct gcagtattgg cagcagtgac tttatttgtt      60
ctatcggtag atcgtggtgt tatagcagat agttttctg ctaatcaaga gattagatat      120
tcggaagtaa caccttatca cgttacttcc gtttggacca aaggagttac tcctccagca      180
aacttcactc aaggtgaaga tgtttttcac gctccttatg ttgctaacca aggatggtat      240
gatattacca aaacattcaa tggaaaagac gatcttcttt gcggggctgc cacagcaggg      300
aatatgcttc actggtggtt cgatcaaaac aaagaccaaa ttaaacgtta tttggaagag      360
catccagaaa agcaaaaaat aaacttcaat ggcgaacaga tgtttgacgt aaaagaagct      420
atcgacacta aaaccacca gctagatagt aaattatttg aatattttaa agaaaaagct      480
ttcccttatc tatctactaa cacctagga gttttccctg atcatgtaat tgatatgttc      540
attaacggct accgcttag tctaactaac cacggtccaa cgccagtaaa agaaggtagt      600
aaagatcccc gaggtggtat ttttgacgcc gtatttacaa gaggtgatca agtaagcta      660 ttgacaagtc gtcatgattt taagaaaaaa aatctcaaag aaatcagtga tctcattaag      720
```

-continued

| | |
|---|---|
| aaagagttaa ccgaaggcaa ggctctaggc ctatcacaca cctacgctaa cgtacgcatc | 780 |
| aaccatgtta taaacctgtg gggagctgac tttgattcta acgggaacct taaagctatt | 840 |
| tatgtaacag actctgatag taatgcatct attggtatga agaaatactt tgttggtgtt | 900 |
| aattccgctg gaaaagtagc tatttctgct aagaaataa aagaagataa tattggtgct | 960 |
| caagtactag ggttatttac actttcaaca gggcaagata gttggaatca gaccaattaa | 1020 |

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
cgttacttcc gtttggatcc aagg                                          24

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 5
gaaatagcta cttctcgagc ggaatt                                        26

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
tcggtagatc gtgggatcct agcagatagt                                    30

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 7
cggaattctt aattggtctg attccaac                                      28

<210> SEQ ID NO 8
<211> LENGTH: 8
<212> TYPE: PRT
<213> ORGANISM: Homo sapiens

<400> SEQUENCE: 8

Gly Pro Ser Val Phe Leu Phe Pro
1               5

<210> SEQ ID NO 9
<211> LENGTH: 11
<212> TYPE: PRT
<213> ORGANISM: S.Pyogenes

-continued

```
<400> SEQUENCE: 9

Asp Ser Phe Ser Ala Asn Gln Glu Ile Arg Tyr
1               5                   10

<210> SEQ ID NO 10
<211> LENGTH: 6
<212> TYPE: PRT
<213> ORGANISM: Bacteria
<220> FEATURE:
<221> NAME/KEY: Xaa
<222> LOCATION: (1)..(6)
<223> OTHER INFORMATION: ANY AMINO ACID

<400> SEQUENCE: 10

Leu Pro Xaa Thr Gly Xaa
1               5
```